United States Patent
Heitsch et al.

[11] Patent Number: 5,604,251
[45] Date of Patent: Feb. 18, 1997

[54] IMIDAZOLE DERIVATIVES WITH A BIPHENYLSULFONYLUREA OR BIPHENYLSULFONYLURETHANE SIDE CHAIN AND THEIR USE AS ANGITENSIN II RECEPTORS

[75] Inventors: Holger Heitsch, Hofheim am Taunus; Rainer Henning; Adalbert Wagner, both of Hattersheim am Main; Hermann Gerhards, Hofheim am Main; Reinhard Becker, Wiesbaden; Bernward Schölkens, Kelkheim, all of Germany

[73] Assignee: Hoechst Aktiengesellschaft, Frankfurt am Main, Germany

[21] Appl. No.: 479,561

[22] Filed: Jun. 7, 1995

Related U.S. Application Data

[63] Continuation of Ser. No. 26,030, Mar. 4, 1993, abandoned.

[30] Foreign Application Priority Data

Mar. 7, 1992 [DE] Germany .............. 42 07 241.7

[51] Int. Cl.[6] ........... A61K 31/505; A61K 31/415; A61K 31/42; C07D 403/12; C07D 403/14
[52] U.S. Cl. ............. 514/396; 514/275; 514/380; 514/381; 514/392; 514/397; 514/325.1; 514/331.1; 548/316.4; 548/323.5; 548/323.1; 548/325.1; 548/331.1
[58] Field of Search .............. 548/323.5, 216.4; 514/275, 380, 381, 392, 396, 397

[56] References Cited

U.S. PATENT DOCUMENTS

| | | | |
|---|---|---|---|
| 4,355,044 | 10/1982 | Heller | 424/319 |
| 5,064,825 | 11/1991 | Chakravarty et al. | 514/221 |
| 5,087,634 | 2/1992 | Reitz et al. | 548/323.5 X |
| 5,126,342 | 6/1992 | Chakravarty et al. | 514/235.8 |
| 5,128,355 | 7/1992 | Carini et al. | 514/381 |
| 5,135,197 | 8/1992 | Kelley et al. | 248/551 |
| 5,138,069 | 8/1992 | Carini et al. | 548/253 |
| 5,155,118 | 10/1992 | Carini et al. | 514/381 |
| 5,236,928 | 8/1993 | Chakravarty et al. | 548/323.5 X |

FOREIGN PATENT DOCUMENTS

| | | | |
|---|---|---|---|
| 0028834B1 | 1/1984 | European Pat. Off. | C07D 233/68 |
| 0253310A3 | 1/1988 | European Pat. Off. | C07D 233/68 |
| 0323841A3 | 7/1989 | European Pat. Off. | C07D 249/02 |
| 0324377A3 | 7/1989 | European Pat. Off. | C07D 233/64 |
| 0401030 | 12/1990 | European Pat. Off. | |
| 0479479 | 4/1992 | European Pat. Off. | |
| 0503162A1 | 9/1992 | European Pat. Off. | C07D 233/90 |
| 4010797 | 10/1991 | Germany | 548/316.4 |

OTHER PUBLICATIONS

CA 115:29326q, Substituted imidazo–fused 6–membered heterocycles as angiotensin II antagonists, Chakravarty et al., p. 778, 1991.
Remington's Pharmaceitical Sciences, 17th Edition, Chapter 76, pp. 1418–1419 (1985).
Dr. J. Mathieu et al., "Nucleofuger und elektrofuger Austritt," Angew. Chem., vol. 72, pp. 71–74 (1960).
G. Labbé, "Decomposition And Addition Reactions Of Organic Azides," Chem. Rev. 69, p. 345 (1969).

Primary Examiner—Floyd D. Higel
Attorney, Agent, or Firm—Finnegan, Henderson, Farabow, Garrett & Dunner, L.L.P.

[57] ABSTRACT

Imidazole derivatives with a biphenylsulfonylurea or biphenylsulfonylurethane side chain, process for their preparation and their use Compounds of the formula (I)

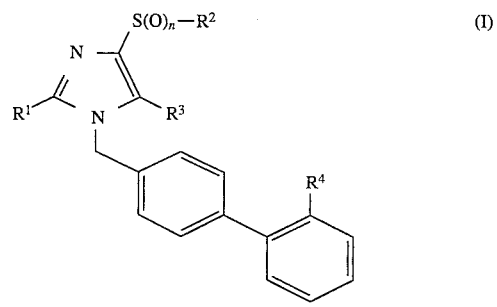

in which
$R^1$ is, for example, ethyl,
$R^2$ is, for example, methyl,
n is, for example, zero,
$R^3$ is, for example, COOH, and
$R^4$ is, for example, $SO_2NHCONHCH_3$
are highly active antagonists of angiotensin II receptors.

12 Claims, No Drawings

IMIDAZOLE DERIVATIVES WITH A BIPHENYLSULFONYLUREA OR BIPHENYLSULFONYLURETHANE SIDE CHAIN AND THEIR USE AS ANGITENSIN II RECEPTORS

This application is a continuation of application Ser. No. 08/026,030, filed Mar. 4, 1993, now abandoned.

The development of novel angiotensin II receptor antagonists is attached growing importance with respect to the provision of novel active substances. EP-A-28834 discloses, for example, 1-benzyl-substituted imidazole derivatives, EP-A-253,310 discloses imidazole derivatives having a diarylcarboxylic acid function and EP-A-324,377 discloses imidazole derivatives having a diaryltetrazolyl group and their use as antagonists of angiotensin II receptors.

Furthermore, 2-n-butyl-substituted imidazole derivatives which have a biphenylsulfonylurea or a biphenylsulfonylurethane structure and their use as antagonists of angiotensin II receptors are presented in EP-A 0,503,162.

In the present invention, novel imidazole derivatives having a biphenylsulfonylurea or biphenylsulfonylurethane side chain are described which, in position 2 of the imidazole ring, have a specific substituent $R^1$ and are surprisingly highly effective angiotensin II receptor antagonists in vitro and in vivo.

The invention relates to compounds of the formula (I)

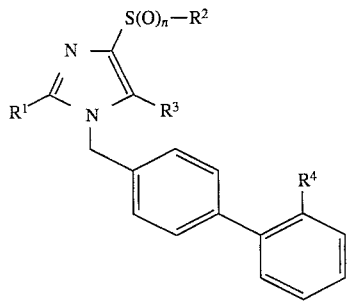

in which the symbols have the following meaning:

a) $R^1$ is $(C_1-C_3)$-alkyl, preferably n-propyl or ethyl, but in particular n-propyl;

b) $R^2$ is
1. $(C_1-C_6)$-alkyl, preferably methyl,
2. $(C_3-C_7)$-cycloalkyl,
3. phenyl or
4. benzyl;

c) $R^3$ is
1. hydrogen,
2. $CH_2OR^5$,
3. $CO-R^6$ or
4. $O-R^7$;

d) $R^4$ is
1. $SO_2NR^7R^8$,
2. $SO_2-NR^8-CO-NR^7R^9$,
3. $SO_2-NH-COO-R^7$,
4. $SO_2-NH-SO_2-NR^7R^9$,
5. $SO_2-NH-CO-R^7$,
6. $SO_2-NH-SO_2-R^7$ or
7. $SO_2N=CH-N(CH_3)_2$;

e) $R^5$ is
1. hydrogen or
2. $(C_1-C_6)$-alkyl;

f) $R^6$ is
1. hydrogen or
2. $OR^7$;

g) $R^7$ and $R^9$ are identical or different and are
1. hydrogen,
2. $(C_1-C_6)$-alkyl, preferably methyl, ethyl or propyl,
3. $(C_3-C_8)$-cycloalkyl,
4. $(C_3-C_6)$-cycloalkyl-$(C_1-C_3)$-alkyl,
5. $(C_6-C_{12})$-aryl, preferably phenyl,
6. $(C_6-C_{10})$-aryl-$(C_1-C_4)$-alkyl, preferably benzyl,
7. $(C_1-C_9)$-heteroaryl, which can be partially or completely hydrogenated,
8. $(C_1-C_9)$-heteroaryl-$(C_1-C_3)$-alkyl, where the heteroaryl moiety can be partially or completely hydrogenated,
9. a radical defined as above in 5., 6., 7. and 8., substituted by 1 or 2 identical or different radicals from the series comprising halogen, hydroxyl, $(C_1-C_4)$-alkyl, methoxy, nitro and cyano,
10. $(C_2-C_6)$-alkenyl or $(C_3-C_6)$-alkenoyl,
11. $(C_3-C_8)$-cycloalkenyl,
12. $(C_3-C_8)$-cycloalkenyl-$(C_1-C_3)$-alkyl,
13. $(C_6-C_{10})$-aryl-$(C_3-C_6)$-alkenyl,
14. $(C_1-C_9)$-heteroaryl-$(C_3-C_6)$-alkenyl and
15. $(C_3-C_6)$-alkynyl;

h) $R^8$ is hydrogen;

i) n is 0, 1 or 2;

and their physiologically tolerable salts.

A preferred compound of the formula (I) is one in which $R^1$ is ethyl or n-propyl, or its physiologically tolerable salts. In particular, $R^1$ is n-propyl.

A preferred compound of the formula (I) is one in which $R^2$ is $(C_1-C_6)$-alkyl, $R^3$ is $COR^6$, N is equal to zero, $R^4$ is $SO_2-NH-CO-OR^7$, $SO_2NHCO-NHR^7$ or $SO_2-NH-CO-R^7$, $R^6$ is hydrogen or $R^7$, and $R^7$ is equal to hydrogen or $(C_1-C_6)$-alkyl, and its physiologically tolerable salts.

Alkyl, alkenyl and alkynyl can be straight-chain or branched.

Cycloalkyl is also understood as meaning alkyl-substituted rings.

$(C_6-C_{12})$-Aryl is, for example, phenyl, naphthyl or biphenyl, preferably phenyl.

$(C_1-C_9)$-Heteroaryl is in particular understood as meaning radicals which are derived from phenyl or naphthyl in which one or more CH groups are replaced by N and/or in which at least two adjacent CH groups are replaced by S, NH or O (with the formation of a five-membered aromatic ring). In addition, one or two atoms of the condensation position of bicyclic radicals (as in indolizinyl) can also be nitrogen atoms.

Heteroaryl is in particular furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isochinolyl, phthalazinyl, quinoxalinyl, quinazolinyl, cinnolinyl.

Stereocenters which may be present can have both the (R)- and the (S)-configuration.

Physiologically tolerable salts of compounds of the formula (I) are understood as meaning both their organic and inorganic salts, as are described in Remington's Pharmaceutical Sciences (17th edition, page 1418 (1985)). Owing to the physical and chemical stability and the solubility, for acidic groups, inter alia, sodium, potassium, calcium and ammonium salts are preferred; for basic groups, inter alia, salts of hydrochloric acid, sulfuric acid and phosphoric acid or of carboxylic acid or sulfonic acids, such as, for example, acetic acid, citric acid, benzoic acid, maleic acid, fumaric acid, tartaric acid and p-toluenesulfonic acid are preferred.

The invention also relates to a process for the preparation of the novel compounds of the formula (I), and their physiologically tolerable salts, which comprises alkylating compounds of the formula (II)

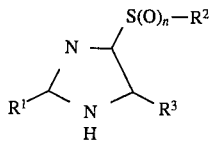

(II)

in which $R^1$, $R^2$, $R^3$ and n are as defined above, with compounds of the formula (III)

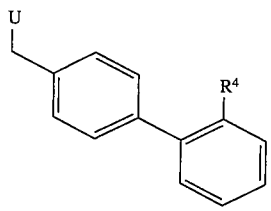

(III)

in which $R^4$ is defined as above and U is a leaving group, optionally removing temporarily introduced protective groups again, optionally converting sulfonamides of the formula (I) obtained into urethanes of the formula (I), optionally converting Sulfonamides of the formula (I) obtained into sulfonylureas of the formula (I) and optionally converting the compounds of the formula (I) obtained into their physiologically tolerable salts.

Suitable leaving groups U are preferably nucleofugic groups (see Angew. Chem. 72 [1960]71) such as halogen, o-toluenesulfonate, mesylate or triflate.

Processes for the preparation of the precursors of the formula (II) are known, inter alia, from U.S. Pat. No. 4,355,044 and EP-A-324,377 and EP-A-323,841 already mentioned above.

Further processes are described by G. L'abbe (Chem. Rev. 69, 345 (1969)), T. Srodsky ("The Chemistry of the Azido Group", Wiley, New York, 1971, p. 331), H. Wamhoff ("Comprehensive Heterocyclic Chemistry") and by P. Katritzky (Ed., Pergamon Press, New York (1984)).

Another process for the preparation of compounds of the formula (II) starts from 1-cyanoglyoxylic acid-2-oxime derivatives and, after reduction of the oxime using reductants known from the literature and addition of mercapto compounds to the nitrile group using suitable protective groups, yields precursors which can be cyclized to imidazoles under water-eliminating conditions. For the cyclization step, inter alia, mixtures of $PCl_5$ and dimethylaminopyridine (DMAP), $POCl_3$ and $SOCl_2$ and their mixtures with DMAP can be used.

For the alkylation of the compounds of the formula (II), for example, appropriate benzyl halides, tosylates, mesylates or triflates or appropriate alkyl halides, tosylates, mesylates or triflates are suitable.

These compounds are prepared in a manner known per se, for example by halogenation of the corresponding methyl precursors. N-bromosuccinimide is preferably employed for this purpose, see, for example, J. Org. Chem. 44, 4733 (1979) and Helv. Chim. Acta 62, 2661 (1979).

The biphenyl derivatives can be synthesized, for example, starting from arylboronic acid derivatives, by coupling with substituted aryl halides using transition metal catalysts, in particular palladium. Appropriate reactions are described by R. B. Miller et al. (Organometallics 1984, 3, 1261) or by A. Zuzuki et al. (Synthetic Commun. 11 (7), 513 (1981)).

The sulfonylurethane derivatives of the formula (I) can be obtained from corresponding sulfonamides of the formula (I) by reaction with chlorocarbonic acid esters and bases such as, for example, potassium carbonate in inert solvents, preferably at temperatures up to the boiling point of the appropriate solvent.

The sulfonylurea derivatives of the formula (I) can be prepared alternatively either from the corresponding sulfonamides of the formula (I) by reaction with isocyanates or with 2,2,2-trichloroacetamide derivatives of a suitable amine in inert, high-boiling solvents such as, for example, DMSO or from sulfonylurethanes of the formula (I) by action of the corresponding amine in an inert, high-boiling solvent such as, for example, toluene at temperatures up to the boiling point of the respective solvent.

Analogously, sulfonylsulfonamides can be prepared from the corresponding sulfonamides by reaction with sulfonyl chlorides or sulfamoyl chlorides.

If necessary, the sulfonamide radical can be prepared starting from an amino group by means of Meerwein rearrangement. For this purpose, the hydrochloride of the amine is first diazotized and then reacted with sulfur dioxide in glacial acetic acid in the presence of a copper catalyst. Subsequent action of ammonia leads to the sulfonamido group.

The sulfonamido group is, for example, temporarily protected by conversion into the 2-N,N-dimethylaminoformylsulfonamido group. This conversion is alternatively carried out either by reaction of the corresponding sulfonamide compound with N,N-dimethylformamide dimethyl acetal or by conversion of the corresponding sulfonamide compound with N,N-dimethylformamide in the presence of dehydrating agents such as $SOCl_3$, $POCl_3$, $PCl_5$ or ethyl chloroformate.

This protective group can be removed both under basic and acidic conditions.

Alternatively, an appropriate thiophenol can be converted into a sulfonamide by oxidation with chlorine and subsequent action of ammonia.

Alkylation is carried out according to methods known in principle in an analogous manner.

Imidazoles of the formula (II) are metallated, for example, in the presence of a base. Preferred bases are metal hydrides such as lithium hydride, sodium hydride or potassium hydride in, for example, DMF or DMSO as solvent or metal alkoxides of the formula MOR, where R is methyl, ethyl or t-butyl, and the reaction is carried out in the corresponding alcohol, DMF or DMSO. The salts of the imidazo derivatives formed in this way are dissolved in an aprotic solvent such as DMF or DMSO and treated with a suitable amount of alkylating reagent.

An alternative possibility for the deprotonation of the imidazole derivatives is, for example, reaction with potassium carbonate in DMF or DMSO.

The thio compounds of the formula (I) where n=0 are preferably oxidized to the corresponding sulfones (n=1) and sulfoxides (n=2) by peracids in suitable solvents such as, for example, $CH_2Cl_2$.

The reactions are carried out at temperatures below room temperature up to the boiling point of the reaction mixture, preferably between +20° C. and the boiling point of the reaction mixture, for about 1 to 10 hours.

The compounds of the formula (I) according to the invention have antagonistic action on angiotensin II receptors and can therefore be used, for example, for the treatment of angiotensin II-dependent hypertension. Possibilities of application furthermore exist in cardiac insufficiency, cardioprotection, myocardial infarkt, cardiacohypertrophy, arteriosclerosis, nephropathy, kidney failure and cardiovascular disorders of the brain such as transitory ischemic attacks and stroke.

Renin is a proteolytic enzym of the aspartyl protease class, which, as a consequence of various stimuli (volume depletion, sodium deficiency, β-receptor stimulation), is secreted into the blood circulation by the juxtaglomerular cells of the kidney. It there cleaves the decapeptide angiotensin I from the angiotensinogen excreted from the liver. This is converted into angiotensin II by the "angiotensin-converting enzyme" (ACE). Angiotensin II plays an essential role in blood pressure regulation, as it directly increases the blood pressure by means of vasoconstriction. In addition, it stimulates the secretion of aldosterone from the adrenal gland and in this way increases the extracellular fluid volume via the inhibition of sodium excretion, which in turn contributes to a blood pressure increase.

Post-receptor actions are, inter alia, stimulation of phosphoinositol conversion ($Ca^{2+}$ release), activation of protein kinase C and facilitation of c-AMP-dependent hormone receptors.

The affinity of the compounds of the formula (I) for the angiotensin II receptor can be determined by measurement of $^{125}I$-angiotensin II or $^{3}H$-angiotensin II displacement from receptors on membranes of the zona glomerulosa of bovine adrenal glands. For this, the prepared membranes are suspended in buffer at pH 7.4.

In order to prevent the degradation of the radioligand during the incubation, aprotinin, a peptidase inhibitor, is added. In addition, about 14,000 cpm of a tracer having a specific activity of 74 TBq/mmol (commercially available from Amersham Buchler, Brunswick, FRG) and an amount of receptor protein which binds 50% of the tracer are used. The reaction is started by addition of 50 μl of membrane suspension to a mixture of 100 μl of buffer+aprotinin, 50 μl of buffer with or without angiotensin II or receptor antagonist and 50 μl of tracer. After an incubation time of 60 minutes at a temperature of 25° C., bound and free radioligand are separated by a filtration assay (for example with Whatman® GFIC filters on a Skatron® cell collector).

Non-specific binding is prevented by treatment of the filter with 0.3% polyethylenimine pH=10 (for example Sigma, No. 3143). By measurement of the radioactivity in a gamma scintillation counter, the strength of displacement of the radioligand from the receptor is determined.

The $IC_{50}$ values, which are the concentration of inhibitor to displace 50% of the ligand, are determined according to J. Theor. Biol. 59, 253 (1970). For the compounds of the formula (I), they are in the range from $1\times10^{-4}$ to $1\times10^{-9}$M.

Alternatively, the affinity of the compounds of the formula (I) for the angiotensin II receptor can be determined by measurement of the $^{125}I$-angiotensin II or $^{3}H$-angiotensin II displacement of receptor preparations from various organs (liver, lung, adrenal gland, brain, etc.).

For this purpose, the prepared membranes are suspended in an incubation buffer (for example 20 mM tris, pH 7.4, containing 135 mM NaCl, 10 mM KCl, 10 mM $MgCl_2$, 5 mM glucose, 0.2% of bovine serum albumin and the protease inhibitors PMSF 0.3 mM and bacitracin 0.1 mM) and incubated at 25° C. for 90 min. together with the radiolabeled angiotensin II and various concentrations of the compounds to be tested. Bound and free radioligand are then separated by filtration through micro glass fiber filters (for example GF51, Schleicher & Schüll on a cell collector (SKATRON)).

By measurement of the receptor-bound radioactivity on the filters by means of a beta or gamma spectrometer, the degree of displacement of the radioligands from the receptor by the test compounds is determined. The strength of the displacement of the radioligand from the receptor by the test compounds is indicated by the $IC_{50}$, i.e. the concentration of the inhibitor which displaces 50% of the bound radioligand from the receptor. The $IC_{50}$ values are calculated by means of PC software (for example LIGAND, G. A. McPherson 1985, Elsevier-BIOSOFT, 68 Hills Road, Cambridge CB 2 1LA, U.K.). The $IC_{50}$ values measured for compounds of the formula (I) are in the range from $1\times10^{-5}$ to $1\times10^{-11}$M.

To determine the antagonistic action of the compounds of the formula (I) in vivo, their inhibiting effect on the angiotensin II-induced blood pressure increase in emedullated Sprague-Dawley rats (Möllegard, Denmark) can be measured. Intravenous administration is carried out in the penis vein.

After preparation of the animal and a waiting time of 20 minutes to stabilize the hemodynamic parameters, 3 successive injections of 10, 30 and 100 mg of angiotensin II in 0.1 ml of aqueous solution are administered at 5 minute intervals. The compounds of the formula I are. dissolved in distilled water, if necessary with addition of 10% strength ethanol and/or bases (pH<10) or acids (pH>3), and administered intravenously in doses of 1–300 μg/kg or intraduodenally in doses of 5–1000 μg/kg.

In the case of intraduodenal administration, the angiotensin II injection is carried out after 20, 40 and 60 minutes, while in the case of intravenous administration the pressor response sequence takes place at 10 minute intervals.

The compounds of the formula (I) are intravenously active, in particular in the range 1–300 μg/kg or intraduodenally active, in particular in the range 5–300 μg/kg.

The invention also relates to pharmaceutical preparations consisting essentially of a compound of the formula (I) and if desired other active substances, such as, for example, diuretics or non-steroidal anti-inflammatory active substances. The compounds of the formula (I) can also be used as diagnostics for the renin-angiotensin system.

Pharmaceutical preparations contain an effective amount of the active substance of the formula (I) and if necessary other active substances together with an inorganic or organic pharmaceutically utilizable excipient and if appropriate further additives or auxiliaries. Administration can be carried out intranasally, intravenously, subcutaneously or orally. The dose of the active substance depends on the warm-blooded animal species, the body weight, the age and the manner of administration.

The pharmaceutical preparations of the present invention are prepared in a dissolving, mixing, granulating or coating process known per se.

For an oral administration form, the active compounds are mixed with the additives customary therefore, such as excipients, stabilizers or inert diluents, and brought by customary methods into suitable administration forms such as tablets, coated tablets, hard gelatine capsules, aqueous, alcoholic or oily suspensions or aqueous, alcoholic or oily solutions. Inert exipients which can be used are, for example, gum arabic, magnesia, magnesium carbonate, potassium phosphate, lactose, glucose, magnesium stearyl fumarate or starch, in particular cornstarch. Preparation here can take place as dry or moist granules. Possible oily exipients or solvents are, for example, vegetable or animal oils, such as sunflower oil and fish liver oil.

For subcutaneous or intravenous administration, the active compounds or their physiologically tolerable salts are brought into solutions, suspensions or emulsions, if appropriate using the substances customary therefore, such as solubilizers, emulisifiers or further auxiliaries. Suitable solvents are, for example, water, physiological saline solution or alcohols, such as ethanol, propanediol or glycerol, and also sugar solutions such as glucose or mannitol solutions or mixtures of the solvents mentioned.

List of abbreviations:

Ac Acetyl

DMF N,N-Dimethylformamide

DME Dimethoxyethane

EA Ethyl acetate

DCI Desorption-Chemical Ionisation

FAB Fast Atom Bombardment

RT Room Temperature

M.p. Melting Point h hour(s)

min. Minute(s)

The invention is illustrated by the following examples:

EXAMPLE 1

Ethyl 1-[(2'-n-propylaminocarbonylaminosulfonylbiphenyl-4-yl)methyl]-2-n-propyl-4-methylthioimidazole-5-carboxylate

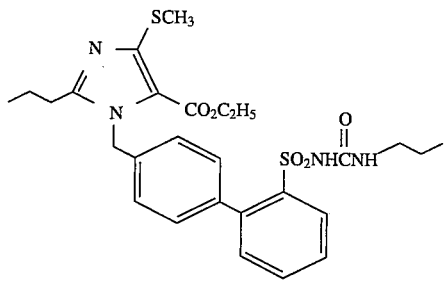

a) Ethyl 2-amino-2-cyanoacetate 228 g (1.3 mol) of sodium dithionite are added at RT in portions in the course of 20 min. to 70 g (0.492 mol) of ethyl 2-cyanoglyoxylate-2-oxime in 700 ml of water and 560 ml of saturated $NaHCO_3$ solution. The mixture is stirred at 35° C. for 12 h and, after cooling and saturation with NaCl, extracted with $CH_2Cl_2$. Drying with $Na_2SO_4$ and concentration to dryness yields 30 g of the title compound as an oil.

Rf ($CH_2Cl_2/CH_3OH$ 9:1)=0.6.

b) Ethyl 2-cyano-2-n-propylcarbonylaminoacetate

A solution of 24.2 ml (0.23 mol) of butyryl chloride in 25 ml of $CH_2Cl_2$ is added dropwise at 0°–5° C. to 30 g. (0.233 mol) of the compound from 1a) in 250 ml of abs. $CH_2Cl_2$ and 18.9 ml (0.233 mol) of pyridine. The mixture is then stirred at RT for 12 h. The organic phase is washed 3× with $H_2O$ and 1× with saturated NaCl solution, dried using $Na_2SO_4$ and concentrated. Crystallization from diisopropyl ether yields 29.5 g of the title compound.

Rf ($CH_2Cl_2/MeOH$ 9:1)=0.7

M.p. 106° C.

c) Ethyl 3-amino-2-n-propylcarbonylamino-3-methylthioacrylate 14.3 g (0.297 mol) of condensed methyl mercaptan are added at RT to 29.5 g (0.149 mol) of the compound from 1b) and 2.05 ml (0.0145 mol) of triethylamine in 500 ml of ethanol. After allowing to stand at RT for 4 days, the solvent is removed and the residue is crystallized from diisopropyl ether, giving 36.2 g of the title compound.

Rf ($CH_2Cl_2$/Min.9:1)=0.4

M.p. 119° C.

d) Ethyl 2-n-propyl-4-methylthioimidazole-5-carboxylate 19.3 g (0.157 mol) of 4-dimethylaminopyridine in 120 ml of $CH_2Cl_2$ are added dropwise at –78° C. to 29.16 g (0.142 mol) of phosphorus pentachloride in 240 ml of $CH_2Cl_2$. After 10 min., 17.6 g (0.071 mol) of the compound from 1c) in 200 ml of $CH_2Cl_2$ are added dropwise. The mixture is warmed to RT and stirred at RT for 2.5 h. 1.6 l of 1N $NaHCO_3$ solution are then added with ice-cooling, and the mixture is stirred for 1 h and allowed to stand overnight. After separation of the phases, the aqueous phase is extracted 3× with EA, and the combined organic phases are dried using $Na_2SO_4$ and concentrated. Chromatography on $SiO_2$ using $CH_2Cl_2$/EA 4:1 yields 5.6 g of the title compound as an oil.

Rf ($CH_2Cl_2$/EA 4:1)=0.4

MS (DCI): 229(M+H).

e) Sulfonamidobromobenzene 51.6 g (0.3 mol) of o-bromoaniline are added under an argon atmosphere to a solution of 100 ml of conc. HCl and 30 ml of glacial acetic acid, a solution of 22.4 g of sodium nitrite in 30 ml of water is added dropwise at –10° C. and the reaction solution is stirred at –5° C. for 60 min. The solution obtained is added dropwise to a solution of 7 g of $CuCl_2×2H_2O$ and 0.5 g of CuCl in 300 ml of glacial acetic acid saturated with $SO_2$, the mixture is poured into an ice/water mixture after stirring at room temperature for 60 min and extracted with ether, and the ether extracts are washed with satd. $NaHCO_3$ solution and water, dried over $MgSO_4$ and concentrated. The 67.8 g of sulfonyl chloride compound obtained are treated with 300 ml of conc. ammonia in 500 ml of acetone with cooling. After removal of the acetone, the resulting suspension is diluted with water, and the white crystals which deposit are filtered off with suction, washed with $H_2O$ and dried in a high vacuum. The title compound is employed without further purification in the following reaction.

M.p. 190° C.

f) 2-N,N-Dimethylaminoformylsulfonamidobromobenzene 0.236 mol of the compound from Example 1e) in 150 ml of abs. DMF is stirred at room temperature for 2 h with 40 ml of N,N-dimethylformamide dimethyl acetal. The reaction solution is poured onto 200 ml of 5% strength $NaHSO_4$ solution/ice (1:1), and the precipitate which deposits is filtered off with suction, washed with $H_2O$ and dried in vacuo. 67 g of the title compound are obtained.

M.p. 148° C.,

Rf ($SiO_2$, EA/heptane 1:1)=0.1

MS (DCI): 291/293 (M+H)

g) 4'-Methylbiphenyl-2-N,N-dimethylaminoformylsulfonamide

First 420 mg of Pd(OAc)$_2$ and then 5.66 g (41.9 mmol) of tolylboronic acid in 100 ml of ethanol are added under argon to 11 g (37.9 mmol) of the compound from example 1f), 1 g of triphenylphosphine and 8 g of $Na_2CO_3$ in 150 ml of toluene and 40 ml of $H_2O$. The mixture is now heated to boiling for 4 h, then concentrated and taken up in 500 ml of EA and 500 ml of $H_2O$. The resulting precipitate is filtered off and characterized as title compound. The EA phase is separated, dried over $Na_2SO_4$ and concentrated. Chromatography on $SiO_2$ using EA yields a further amount of the title compound;

Total yield: 7.6 g

M.p. 181°–184° C.

Rf (SiO$_2$, EA/heptane 1:1)=0.2

MS (DCI): 303 (M+H)

h) 4'-Bromomethylbiphenyl-2-N,N-dimethylaminoformyl-sulfonamide 7.4 g (0.025 mol) of the compound from 1 g) are heated to reflux for 2 h with 4.6 g (0.026 mol) of N-bromosuccinimide in 130 ml of chlorobenzene in the presence of 300 mg of benzoyl peroxide. After cooling, 50 ml of saturated Na$_2$SO$_3$ solution are added, and the organic phase is separated, washed with saturated Na$_2$CO$_3$ solution, water and saturated NaCl solution, dried over Na$_2$SO$_4$ and concentrated. The residue is stirred with EA and 6.7 g of the title compound filtered off with suction.

M.p. 168°–171° C.

Rf (SiO$_2$, EA)=0.5

MS (DCI) 381/383 (M+H)

Ethyl 1-[(2'-N,N-dimethylaminoformylsulfonamidobiphenyl-4-yl)methyl]-2-n-propyl-4-methylthioimidazole-5-carboxylate 2.0 g (8.75 mmol) of the compound from 1d), 4.15 g (8.75 mmol) of the compound from 1 h) (75% strength) and 1.25 g ( 9.0 mmol ) of K$_2$CO$_3$ are stirred overnight at RT in 50 ml of abs. DMF. The mixture is concentrated, the residue is dissolved in 400 ml of EA, and the EA solution is washed 3× with water, dried over Na$_2$SO$_4$ and concentrated. The residue is stirred with ethanol and diisopropyl ether and 4.14 g of the title compound are filtered off with suction as the precipitate which deposits.

M.p. 169°–171° C.

Rf (SiO$_2$, EA)=0.4

MS (FAB): 529 (M+H)

j) Ethyl 1-[(2'-sulfonamidobiphenyl-4-yl)methyl]-2-n-propyl-4-methylthioimidazole-5-carboxylate 4 g (7.60 mmol) of the compound from 1i) in 40 ml of methanol are boiled under reflux for 3 h with 20 ml of conc. hydrochloric acid. The mixture is allowed to cool to RT, the solvent is removed by distillation, the pH of the aqueous solution is adjusted to 5–6 with 6N NaOH solution and the mixture is extracted several times with EA. The combined EA phases are dried over Na$_2$SO$_4$ and concentrated. The resulting foam is stirred with ethanol and diisopropyl ether and the precipitate is filtered off with suction. 3 g of the title compound result.

M.p. 125°–127° C.

Rf (SiO$_2$, EA)=0.7

MS (FAB): 474 (M+H)

k) Ethyl 1-[(2'-n-propylaminocarbonylaminosulfonylbiphenyl-4-yl)methyl]-2-n-propyl-4-methylthioimidazole-5-carboxylate 2 g (4.22 mmol) of the compound from 1j) are treated with 1.75 g (12.66 mmol) of anhydrous K$_2$CO$_3$ in 50 ml of abs. acetone. After heating to reflux for 30 min., the solution is treated with 395 μl (4.22 mmol) of propyl isocyanate and stirred under reflux for 1 h. It is then cooled, treated with 15 ml of 2N HCl, concentrated in vacuo and extracted several times with CH$_2$Cl$_2$. Drying over Na$_2$SO$_4$, concentration and crystallization from EA yields 1.9 g of the title compound.

M.p. 160°–165° C.

Rf (SiO$_2$, EA/heptane 2:1)=0.25

MS (FAB): 559 (M+H)

EXAMPLE 2

1-[(2'-n-Propylaminocarbonylaminosulfonylbiphenyl-4-yl)methyl]-2-n-propyl-4-methylthioimidazole-5-carboxylic acid

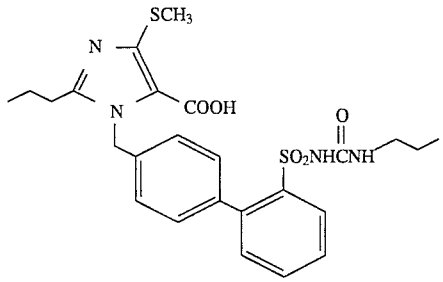

700 mg (1.25 mmol) of the compound from 1k) in 40 ml of methanol are stirred at RT for 3 days with 10 ml of 2N NaOH solution. The solvent is then removed in vacuo, the aqueous solution is adjusted to pH=6 with 2N hydrochloric acid, and the precipitate which desposits is filtered off with suction and dried in a high vacuum. 600 mg of the title compound result.

M.p. 133°–135° C.

Rf (SiO$_2$, CH$_2$Cl$_2$/methanol 10:1)=0.19

MS (FAB): 531 (M+H)

EXAMPLE 3

Ethyl 1-[(2'-ethoxycarbonylaminosulfonylbiphenyl-4-yl)methyl]-2-n-propyl-4-methylthioimidazole-5-carboxylate

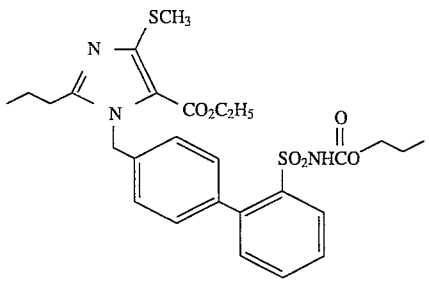

1.5 g ( 3.17 mmol) of the compound from 1j) under an argon atmosphere in 25 ml of abs. DME are boiled under reflux for 3 h with 0.876 g ( 6.34 mmol) of K$_2$CO$_3$ and 0.35 ml (3.17 mmol) of ethyl chloroformate. The solvent is then to the largest extent removed. The pH of the remaining solution is adjusted to about 4 with 10% strength KH$_2$PO$_4$ solution and it is extracted several times with EA. The combined EA extracts are washed with satd. NaCl solution, dried over MgSO$_4$ and concentrated, and the residue is dried in a high vacuum. 1.79 g of the title compound are obtained as a yellow foam.

Rf (SiO$_2$, EA)=0.5

MS (FAB): 546 (M+H)

EXAMPLE 4

1-[(2'-Ethoxycarbonylaminosulfonylbiphenyl-4-yl)methyl]-2-n-propyl-4-methylthioimidazole-5-carboxylic acid

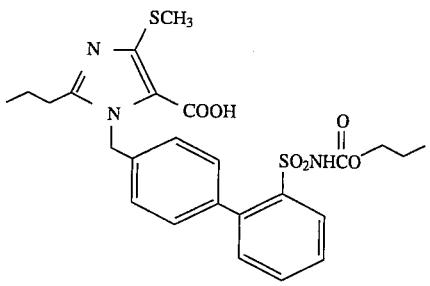

500 mg (0.92 mmol) of the compound from Example 3) in 3 ml of ethanol are stirred at RT for 24 h with 2.5 ml of 2N NaOH solution. The solvent is removed in vacuo, the remaining aqueous solution is adjusted to about pH 5 with 2N hydrochloric acid and the precipitate which deposits is filtered off with suction. 380 mg of the title compound are obtained in the form of a slightly yellow-colored solid product.

M.p. 156°–160° C.

Rf (SiO$_2$, CH$_2$Cl$_2$/CH$_3$OH 9:1)=0.3

MS (FAB): 518 (M+H)

EXAMPLE 5

Ethyl 1-[(2'-methylaminocarbonylaminosulfonylbiphenyl-4-yl)methyl]-2-ethyl-4-methylthioimidazole-4-carboxylate

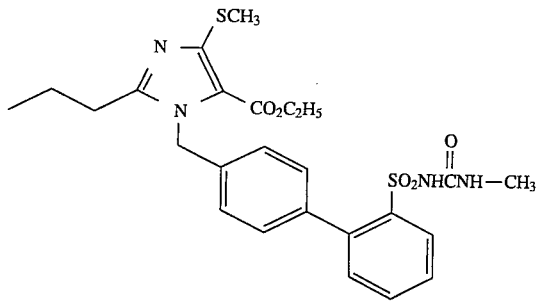

a) Ethyl 2-cyano-2-ethylcarbonylaminoacetate

The title compound is prepared by the method indicated in Example 1b), in this case propionyl chloride instead of butyryl chloride being reacted with the compound from 1a). Starting from 12.8 g (0.1 mol) of the compound from 1a), 11.4 g of the title compound result.

M.p. 111°–113° C.

Rf (SiO$_2$, EA)=0.6

MS (DCI): 185 (M+H)

b) Ethyl 3-amino-2-ethylcarbonylamino-3-methylthioacrylate

This compound is prepared analogously to the method indicated in Example 1c).

M.p. 127° C.

Rf (SiO$_2$, EA)=0.18

MS (DCI): 233 (M+H)

c) Ethyl 2-ethyl-4-methylthioimidazole-5-carboxylate

This compound is prepared analogously to the method given in 1d).

M.p. 141°–143° C.

Rf (SiO$_2$, EA)=0.4

MS (DCI): 215 (M+H)

d) Ethyl 1-[(2'-N,N-dimethylaminoformylsulfonamidobiphenyl-4-yl)-methyl]-2-ethyl-4-methylthioimidazole-5-carboxylate The title compound is prepared from compound 5c) and compound 1h) by the method described in Example 1i).

M.p. 189°–194° C.

Rf (SiO$_2$, EA)=0.3

MS (FAB): 515 (M+H)

Ethyl 1-[(2'-Sulfonamidobiphenyl-4-yl)methyl]-2-ethyl-4-methylthioimidazole-5-carboxylate The title compound is prepared from the compound of Example 5d) by the method of Example 1j).

M.p. 153°–155° C.

Rf (SiO$_2$, EA)=0.5

MS (FAB): 460 (M+H)

f) 2,2,2-Trichloro-N-methylacetamide 1.6 g (51.5 mmol) of methylamine are condensed and treated in 20 ml of abs. dioxane with 7.14 ml (51.5 mmol) of triethylamine and 5.7 ml (51.5 mmol) of trichloroacetyl chloride, dissolved in 10 ml of abs. dioxane, and the resulting solution is stirred at RT for 3 h. It is then treated with water, the pH of the solution is adjusted to about 1 with 2N hydrochloric acid and the title compound which deposits (7.6 g) is filtered off with suction.

M.p. 90°–95° C.

g) Ethyl 1-[(2'-methylamminocarbonylaminosulfonylbiphenyl-4-yl)methyl]-2-ethyl-4-methylthioimadazole-5-carboxylate 135 mg (0.316 mmol) of the compound from 5e) in 2 ml of abs. DMSO are stirred under an argon atmosphere at 80° for 30 min with 38 mg (0.1 mmol) of powdered NaOH and 61 mg (0.348 mmol) of the compound from 5f). The reaction solution is poured onto ice-water, acidified with 2N hydrochloric acid and extracted several times with EA. After washing the combined EA phases with saturated NaCl solution, drying over MgSO$_4$ and concentrating, the crystalline residue obtained is stirred with a little EA. Filtering off the precipitate with suction yields 97 mg of the title compound.

M.p. 220°–223° C.

Rf (SiO$_2$, CH$_2$Cl$_2$/CH$_3$OH 9:1)=0.6

MS (FAB): 517 (M+H)

EXAMPLE 6

1-[(2'-Methylaminocarbonylaminosulfonylbiphenyl-4-yl)methyl]-2-ethyl-4-methylthioimidazole-5-carboxylic acid

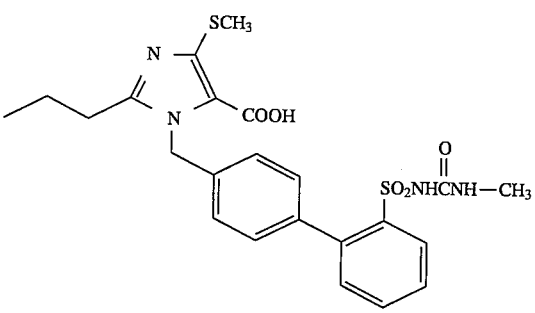

The title compound is prepared from the compound of 5g) by the method of Example 2). Starting from 50 mg (0.1 mmol) of the compound 5g), 40.5 mg of the title compound result.

M.p. 155° C.

Rf (SiO$_2$, CH$_2$Cl$_2$/CH$_3$OH/acetic acid 9:1:0.2)=0.46
MS (FAB): 489 (M+H)

EXAMPLE 7

Ethyl 1-[(2'-ethoxycarbonylaminosulfonylbiphenyl-4-yl)methyl]-2-ethyl-4-methylthioimidazol-5-carboxylate

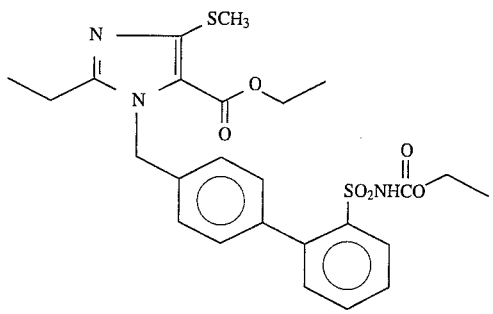

1.4g (3 mmol) of the compound from Example 5e) and 825 mg (6 mmol) of K$_2$CO$_3$ are boiled under reflux for 3 hours in 25 ml abs. DME with 0.3 ml (3.05 mmol) of ethyl chloroformate. The mixture is concentrated, adjusted to pH ~5 with 10% strength KH$_2$PO$_4$ solution and extracted with EA. After drying over Na$_2$SO$_4$ and concentration, 1.45 g of the title compound results.

Rf (SiO$_2$, EA)=0.3
MS (FAB): 532 (M+H)

EXAMPLE 8

Ethyl 1-[2'-n-propylaminocarbonylaminosulfonylbiphenyl-4-yl)methyl]-2-ethyl-4-methylthioimidazol-5-carboxylate

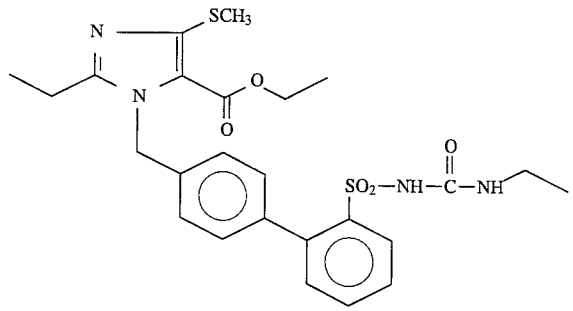

300 mg (0.56 mmol) of the compound from Example 7 are boiled under reflux for 3 hours in 7 ml of abs. toluene with 1.5 ml of n-propylamine. After concentration and chromatography on SiO$_2$ using EA as the eluent, 130 mg of the title compound results.

m.p.: 202°–203° C.,
Rf (SiO$_2$, EA)=0.24
MS (FAB): 545 (M+H)

EXAMPLE 9

1-[(2'-n-propylaminocarbonylaminosulfonylbiphenyl-4-yl)methyl]-2-ethyl-4-methylthioimidazol-5-carboxylic acid

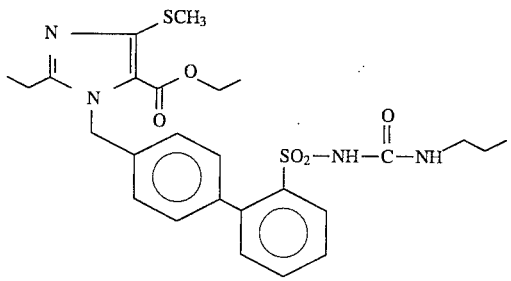

The title compound is prepared from the compound of Example 8) by the method of Example 2). Starting from 100 mg (0.18 mmol) of the compound 8), 70 mg of the title compound result.

m.p.: 135°–140° C.
Rf (SiO$_2$, EA)=0.1
MS (FAB)=517 (M+M)

EXAMPLE 10

1-[(2'-n-propylaminocarbonylaminosulfonylbiphenyl-4-yl)methyl]-2-n-propyl-4-methylsulfonylimidazol-5-carboxylate

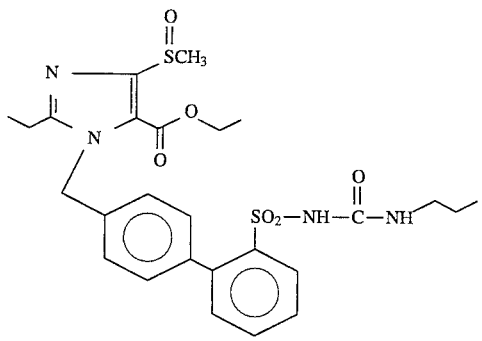

95.0 mg (0.17 mmol) of the compound from Example 1) are stirred for 20 minutes in 10 ml of abs. CH$_2$Cl$_2$ at −78° C. with 59 mg (0.17 mmol) of m-chloroperbenzoic acid (50% strength). The mixture is treated with 10 ml of 10% strength sodiumbisulfite solution, warmed to room temperature and, after phase separation, extracted with EA. The combined organic phases are washed with satd Na$_2$CO$_3$ solution, dried over Na$_2$SO$_4$ and concentrated. 110 mg of the title compound result.

m.p.: 65°–68° C.,
Rf (SiO$_2$, EA)=0.1
MS (FAB): 575 (M+M)

EXAMPLE 11

1-[(2'-n-propylaminocarbonylaminosulfonylbiphenyl-4-yl)methyl-2-n-propyl-4-methylsulfoxylimidazol-5-carboxylic acid

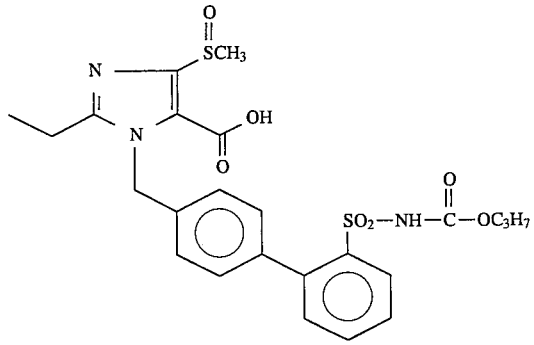

The title compound results from the compound of Example 10) by the method of Example 2). Starting from 100 mg (0.17 mmol) of the compound from Example 10), 83 mg of the title compound are obtained.

m.p.: 105°–108° C.,
Rf (SiO$_2$, EA)=0.1
MS (FAB): 547 (M+M)

EXAMPLE 12

1-[2'-Ethoxycarbonylaminosulfonylbiphenyl-4-yl)methyl]-2-n-propyl-4-methylsulfonylimidazol-5-carboxylate

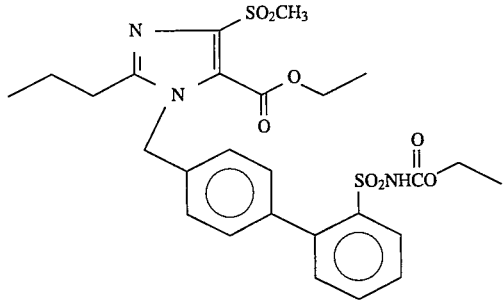

350 mg (0.64 mmol) of the compound from Example 3) are heated under reflux for 1 hour with 443 mg (1.28 mmol) of m-chlorobenzoic acid (50% strength) in 20 ml of abs. CH$_2$Cl$_2$. Working up is carried out analogously to that of Example 10) and yield 364 mg of the title compound as a colorless foam.

Rf (SiO$_2$, CH$_2$Cl$_2$/MeOH 9:1) 0.74,
MS (FAB): 578 (M+H)

EXAMPLE 13

1-[2'-Ethoxycarbonylaminosulfonylbiphenyl-4-yl)methyl]-2-n-propyl-4-methylsulfonylimidazol-5-carboxylic acid

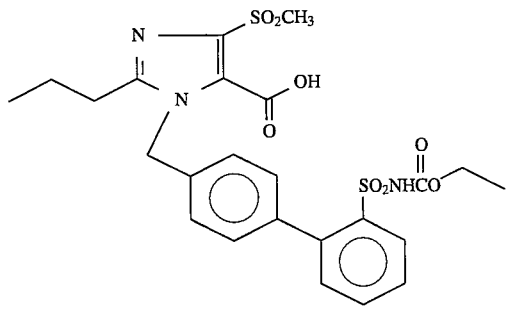

Starting from 120 mg (0.2 mmol) of the compound from Example 12), 84 mg of the title compound results by the method of Example 2).

m.p.: 156°–159° C.,
Rf (SiO$_2$, CH$_2$Cl$_2$/MeOH 9:1:0.2)=0.5
MS (FAB): 550 (M+H)

EXAMPLE 14

1-[2'-Ethylaminocarbonylaminosulfonylbiphenyl-4-yl)-2-n-propyl-4-methylsulfonylimidazol-5-carboxylate

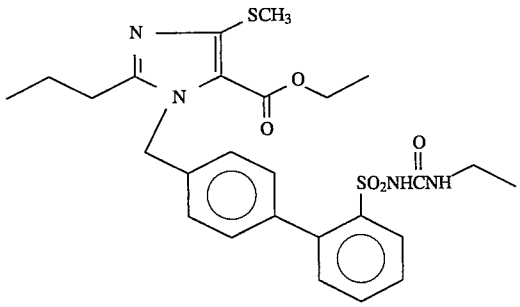

The conversion of 200 mg (0.42 mmol) of the compound from Example 1j) using 34 μl (0.42 mmol) of ethyl isocyanate by the method of Example 1k) yields 17.0 mg of the title compound.

m.p.: 161°–162° C.,

Rf (SiO$_2$, EA)=0.43,

MS (FAB): 545 (M+H)

EXAMPLE 15

1-[(2'-Ethylaminocarbonylaminosulfonylbiphenyl-4-yl)methyl]-2-n-propyl-4-methylsulfonylimidazol-5-carboxylic acid

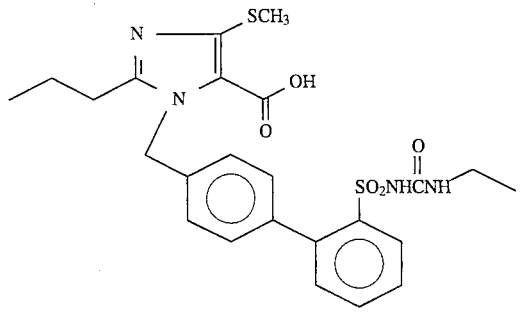

Starting from 61 mg (0.11 mmol) of the compound from Example 14), 56 mg of the title compound result by the process of Example 2).

m.p.: 131° C.,

Rf (SiO$_2$, CH$_2$Cl$_2$lM/eOH 10:1)=0.2

MS (FAB): 517 (M+H)

EXAMPLE 16

1-[2'-Allylaminocarbonylaminosulfonylbiphenyl-4-yl)methyl]-2-n-propyl-4-methylthioimidazol-5-carboxylate

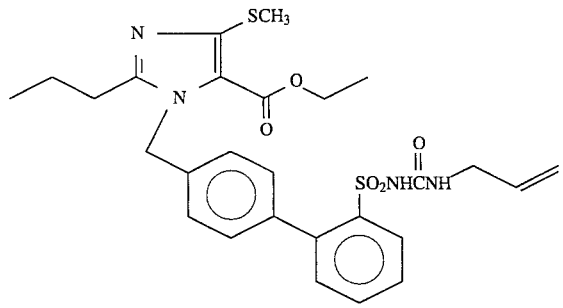

The conversion of 200 mg (0.42 mmol) of the compound from Example 1j) using 38 µl (0.42 mmol) of allyl isocyanate by the method of Example 1k) yields 150 mg of the title compound.

m.p.: 184° C.

Rf (SiO$_2$, EA):0.43,

MS (FAB): 557 (M+H)

EXAMPLE 17

1-[(2'Allylaminocarbonylaminosulfonylbiphenyl-4-yl)methyl]-2-n-propyl-4-methylthioimidazol-5-carboxylic acid

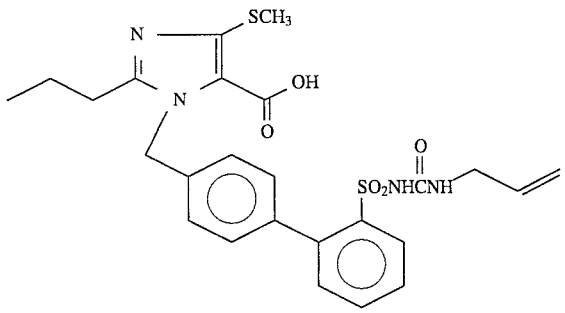

Starting from 60 mg (0.1 mmol) of the compound from Example 16), 54 mg of the title compound result by the method of Example 2).

m.p.: 148° C.,

Rf (SiO$_2$, CH$_2$Cl$_2$/MeOH 10:1):0.3,

MS (FAB): 529 (M+H)

EXAMPLE 18

1-[(2'-Methoxycarbonylaminosulfonylbiphenyl-4-yl)methyl]-2-n-propyl-4-methylthioimidazol-5-carboxylate

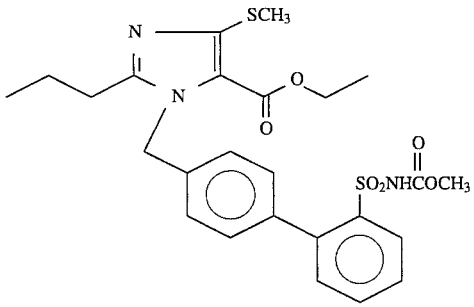

500 mg (1.06 mmol) of the compound from Example 1j) are boiled under reflux for 2 hours with 293 mg (2.12 mmol) of K$_2$CO$_3$, 106 ml (1.06 mmol) of dimethyl dicarbonate and 53 mg of DMAP in 20 ml of diethylene glycol dimethyl ether. The solvent is removed in a rotary evaporator, the residue is treated with EA/KH$_2$PO$_4$ solution, and the organic phase is separated off and concentrated after drying over Na$_2$SO$_4$.

Chromatography on SiO$_2$ (EA/heptane 2:1) yields 225 mg of the title compound.

m.p.: 146° C.,

Rf (SiO$_2$, EA)=0.37,

MS (FAB); 532 (M+H)

EXAMPLE 19

1-[(2'-Methoxycarbonylaminosulfonylbiphenyl-4-yl)methyl]-2-n-propyl-4-methylthioimidazol-5-carboxylic acid

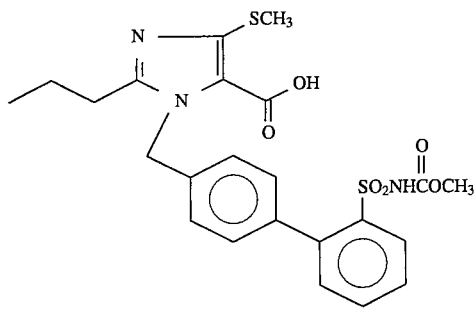

The treatment of 150 mg (0.263 mmol) of the compound from Example 18) analogously to that of Example 2) yields 110 mg of the title compound.

m.p.: 131° C.
Rf (SiO$_2$, CH$_2$Cl$_2$/MeOH 10:1)=0.15,
MS (FAB): 504 (M+H)

EXAMPLE 20

1-[(2'Cyclopropylmethylaminocarbonylamino-sulfonylbiphenyl-4-yl)methyl]-2-n-propyl-4-methylthioimidazol-5-carboxylate

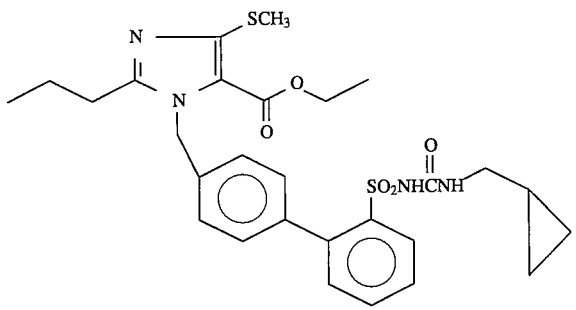

500 mg (1.06 mmol) of the compound from Example 1j) are stirred at room temperature for 2 hours with 408 mg (1.06 mmol) of dihydroxybenzotriazolyl carbonate (70% strength) and 85 ml (1.06 mmol) of pyridine in 20 ml of abs. CH$_2$Cl$_2$. The reaction solution is then stirred again for 2 hours with 114 mg (1.06 mmol) of cyclopropylmethylamine hydrochloride and 170 ml (2.12 mmol) of pyridine.

The mixture is concentrated in a rotary evaporator, the residue is taken up in EA, and the EA phase is washed with NaHCO$_3$ solution and NaHSO$_4$ solution, dried over Na$_2$SO$_4$ and concentrated. Chromatography on SiO$_2$ (EA/heptane 1:3) yields 72 mg of the title compound.

m.p.: 125° C.,
Rf (SiO)$_2$, EA)=0.47,
MS (FAB): 571 (M+H)

EXAMPLE 21

1-[(2'Cyclopropylmethylamminocarbonylamino-sulfonylbiphenyl-4-yl)methyl]-2-n-propyl-4-methylthioimidazol-5-carboxylic acid

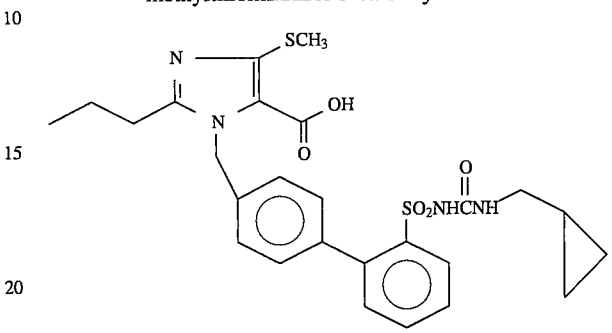

The hydrolysis of 45 mg (0.08 mmol) of the compound from Example 20) analogously to Example 2) yields 34 mg of the title compound.

m.p.: 138° C.,
Rf (SiO$_2$, SiO$_2$, CH$_2$Cl$_2$/MeOH 9:1)=0.1,
MS (FAB): 543 (M+H)

EXAMPLE 22

1-[(2'Propyloxycarbonylaminosulfonylbiphenyl-4-yl)methyl]-2-n-propyl-4-methylthioimidazol-5-carboxylate

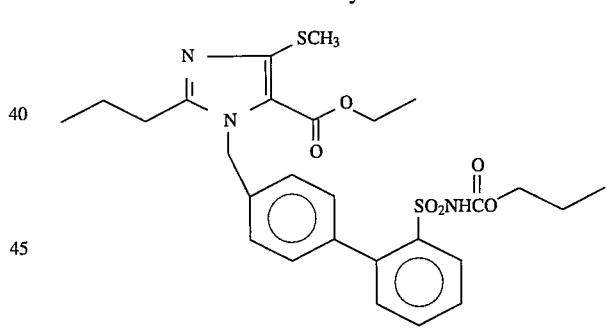

The conversion of 200 mg (0.42 mmol) of the compound from Example 1j) with 70 ml (0.63 mmol) of propyl chloroformate analogously to Example 3) yields 200 mg of the title compound after chromatography on SiO$_2$ (EA/heptane 2:1).

m.p.: 144° C.
Rf (SiO$_2$, EA)=0.54,
MS (FAB): 560 (M+H)

EXAMPLE 23

1-[(2'-Propyloxycarbonylaminosulfonylbiphenyl-4-yl)methyl]-2-n-propyl-4-methylthioimidazol-5-carboxylic acid

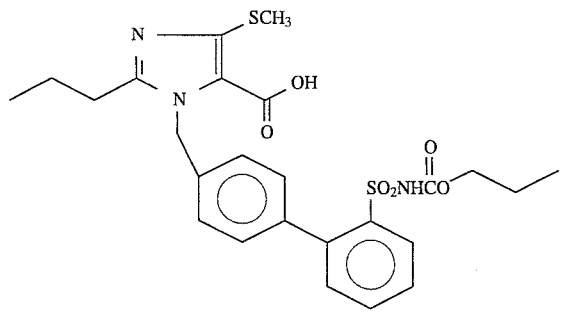

This compound results from the compound of Example 22) by the method of Example 2).

m.p.: 124° C.,
Rf (SiO$_2$, CH$_2$Cl$_2$/MeOH 10:1)=0.1,
MS (FAB); 532 (M+H)

EXAMPLE 24

1-[(2'-Benzyloxycarbonylaminosulfonylbiphenyl-4-yl)methyl]-2-n-propyl-4-methylthioimidazol-5-carboxylate

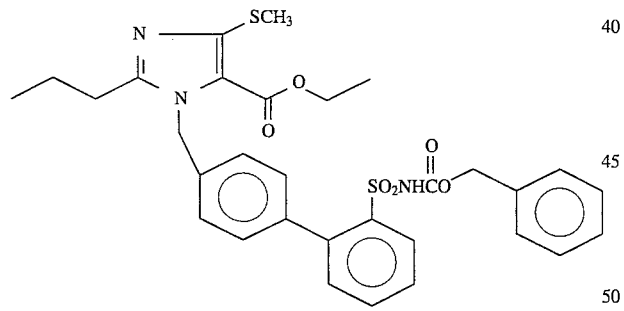

The conversion of 200 mg (0.42 mmol) of the compound from Example 1j) using 89 μl (0.633 mmol) of benzyl chloroformate analogously to Example 3) yields 250 mg of the title compound after chromatography on SiO$_2$ (EA/heptane 2:1).

m.p.: 158° C.,
Rf (SiO$_2$, EA)=0.55,
MS (FAB): 608 (M+H)

EXAMPLE 25

1-[(2'-Benzyloxycarbonylaminosulfonylbiphenyl-4-yl)methyl]-2-n-propyl-4-methylthioimidazol-5-carboxylic acid

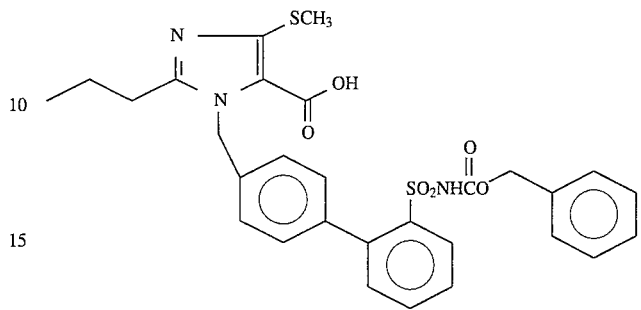

This compound results from the compound of Example 24) by the method of Example 2).

m.p.: 115° C.,
Rf (SiO$_2$, CH$_2$Cl$_2$/MeOH 15:1)=0.1
MS (FAB): 580 (M+H)

We claim:

1. A compound of the formula (I):

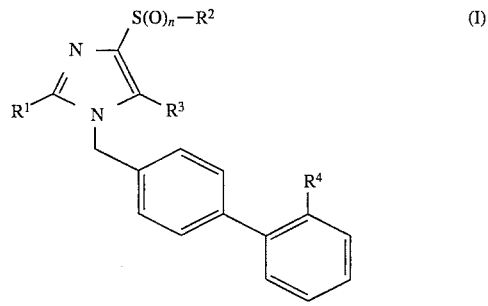

wherein:
a) $R^1$ is (C$_1$–C$_3$)-alkyl;
b) $R^2$ is
 1. (C$_1$–C$_6$)-alkyl,
 2. (C$_3$–C$_7$)-cycloalkyl,
 3. phenyl, or
 4. benzyl;
c) $R^3$ is
 1. hydrogen,
 2. CH$_2$OR$^5$,
 3. CO—R$^6$, or
 4. O—R$^7$;
d) $R^4$ is
 1. SO$_2$NR$^7$R$^8$,
 2. SO$_2$—NR$^8$—CO—NR$^7$R$^9$,
 3. SO$_2$—NH—COO—R$^7$,
 4. SO$_2$—NH—SO$_2$—NR$^7$R$^9$,
 5. SO$_2$—NH—CO—R$^7$,
 6. SO$_2$—NH—SO$_2$—R$^7$, or
 7. SO$_2$N=CH—N(CH$_3$)$_2$;
e) $R^5$ is
 1. hydrogen or
 2. (C$_1$–C$_6$)-alkyl;

f) $R^6$ is
  1. hydrogen or
  2. $OR^7$;
g) $R^7$ and $R^9$ are identical or different and are
  1. hydrogen,
  2. $(C_1-C_6)$-alkyl,
  3. $(C_3-C_8)$-cycloalkyl,
  4. $(C_3-C_6)$-cycloalkyl-$(C_1-C_3)$-alkyl,
  5. $(C_6-C_{12})$-aryl,
  6. $(C_6-C_{10})$-aryl-$(C_1-C_4)$-alkyl,
  7. $(C_1-C_9)$-heteroaryl, which is unhydrogenated, partially hydrogenated, or completely hydrogenated,
  8. $(C_1-C_9)$-heteroaryl-$(C_1-C_3)$-alkyl, where the heteroaryl moiety is unhydrogenated, partially hydrogenated, or completely hydrogenated,
  9. a radical defined as above in g) 5.–8., substituted by 1 or 2 identical or different radicals selected from halogen, hydroxyl, $(C_1-C_4)$-alkyl, methoxy, nitro and cyano,
  10. $(C_2-C_6)$-alkenyl or $(C_3-C_6)$-alkenoyl,
  11. $(C_3-C_8)$-cycloalkenyl,
  12. $(C_3-C_8)$-cycloalkenyl-$(C_1-C_3)$-alkyl,
  13. $(C_6-C_{10})$-aryl-$(C_3-C_6)$-alkenyl,
  14. $(C_1-C_9)$-heteroaryl-$(C_3-C_6)$-alkenyl and
  15. $(C_3-C_6)$-alkynyl;
h) $R^8$ is hydrogen;
i) n is 0, 1 or 2;
a physiologically tolerable salts thereof.

2. A compound or salt thereof as claimed in claim 1, wherein $R^1$ is ethyl or n-propyl.

3. A compound or salt thereof as claimed in claim 2, wherein $R^1$ is n-propyl.

4. A compound or salt thereof as claimed in claim 3, wherein $R^2$ is $(C_1-C_6)$-alkyl,
$R^3$ is $COR^6$,
n is equal to zero,
$R^4$ is $SO_2-NH-CO-OR^7$, $SO_2NR^8CONR^7R^9$, or $SO_2-NH-CO-R^7$,
$R^6$ is hydrogen or $OR^7$, and
$R^7$ is equal to hydrogen or $(C_1-C_6)$-alkyl.

5. A compound or salt thereof as claimed in claim 2, wherein $R^1$ is ethyl,
$R^2$ is $(C_1-C_6)$-alkyl,
$R^3$ is $COR^6$,
n is equal to zero,
$R^4$ is $SO_2-NH-CO-OR^7$, $SONR^8CONR^7R^9$, wherein $R^9$ is hydrogen, or $SO_2-NH-CO-R^7$,
$R^6$ is hydrogen or $OR^7$, and
$R^7$ is equal to hydrogen or $(C_1-C_6)$-alkyl.

6. A compound or salt thereof as claimed in claim 1, wherein $R^2$ is $(C_1-C_6)$-alkyl,
$R^3$ is $COR^6$,
n is equal to zero,
$R^4$ is $SO_2-NH-CO-OR^7$, $SO_2NR^8CONR^7R^9$, wherein $R^9$ is hydrogen, or $SO_2-NH-CO-R^7$,
$R^6$ is hydrogen or $OR^7$, and
$R^7$ is equal to hydrogen or $(C_1-C_6)$-alkyl.

7. A pharmaceutical preparation for the treatment of high blood pressure comprising an effective amount of a compound or salt thereof of claim 1 and a physiological acceptable carrier.

8. A pharmaceutical preparation for the treatment of high blood pressure comprising an effective amount of a compound or salt thereof of claim 3 and a physiological acceptable carrier.

9. A pharmaceutical preparation for the treatment of high blood pressure comprising an effective amount of a compound or salt thereof of claim 4 and a physiological acceptable carrier.

10. A method for the treatment of high blood pressure comprising the step administering to a host in need thereof an effective amount of a compound or salt thereof of claim 1.

11. A method for the treatment of high blood pressure comprising the step administering to a host in need thereof an effective amount of a compound or salt thereof of claim 2.

12. A method for the treatment of high blood pressure comprising the step administering to a host in need thereof an effective amount of a compound or salt thereof of claim 4.

* * * * *

UNITED STATES PATENT AND TRADEMARK OFFICE
CERTIFICATE OF CORRECTION

PATENT NO. : 5,604,251

DATED : February 18, 1997

INVENTOR(S) : Holger HEITSCH et al.

It is certified that error appears in the above-indentified patent and that said Letters Patent is hereby corrected as shown below:

Claim 1, column 23, line 28, before "a physiologically" insert --or-- and "salts" should read --salt--.

Claim 4, column 23, line 39, after "$R^9$," insert --wherein $R^9$ is hydrogen,--.

Claim 5, column 24, line 5, "SO" should read --$SO_2$--.

UNITED STATES PATENT AND TRADEMARK OFFICE
CERTIFICATE OF CORRECTION

PATENT NO. : 5,604,251
DATED : February 18, 1997
INVENTOR(S) : Holger Heitsch et al It is certified that error appears in the above-indentified patent and that said Letters Patent is hereby corrected as shown below:

Claim 7, column 24, line 22, "physiological" should read --physiologically--.

Claim 8, column 24, line 26, "physiological" should read --physiologically--.

Claim 9, column 24, line 30, "physiological" should read --physiologically--.

Signed and Sealed this

Sixteenth Day of September, 1997

Attest:

BRUCE LEHMAN

Attesting Officer

Commissioner of Patents and Trademarks